(12) United States Patent
Amari et al.

(10) Patent No.: US 7,671,066 B2
(45) Date of Patent: Mar. 2, 2010

(54) DERIVATIVES OF 1-PHENYL-2-PYRIDYNYL ALKYLENE ALCOHOLS AS PHOSPHODIESTERASE INHIBITORS

(75) Inventors: Gabriele Amari, Parma (IT); Elisabetta Armani, Parma (IT); Eleonora Ghidini, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 110 days.

(21) Appl. No.: 11/827,673

(22) Filed: Jul. 12, 2007

(65) Prior Publication Data
US 2008/0015226 A1 Jan. 17, 2008

(30) Foreign Application Priority Data
Jul. 14, 2006 (EP) ................... 06014672

(51) Int. Cl.
*A61K 31/44* (2006.01)
*A61K 31/435* (2006.01)
*C07D 213/55* (2006.01)

(52) U.S. Cl. ........................ 514/277; 514/278; 514/357; 546/335; 546/342

(58) Field of Classification Search ................ 546/286, 546/301, 335, 342; 514/277, 278, 357
See application file for complete search history.

*Primary Examiner*—Janet L Andres
*Assistant Examiner*—Binta M Robinson
(74) *Attorney, Agent, or Firm*—Ladas and Parry LLP

(57) ABSTRACT

The invention relates to inhibitors of the phosphodiesterase 4 (PDE4) enzyme. More particularly, the invention relates to compounds that are derivatives of 1-phenyl-2-pyridynyl alkylene alcohols, methods of preparing such compounds, compositions containing them and therapeutic use thereof.

16 Claims, No Drawings

DERIVATIVES OF 1-PHENYL-2-PYRIDYNYL ALKYLENE ALCOHOLS AS PHOSPHODIESTERASE INHIBITORS

FIELD OF THE INVENTION

The present invention relates to inhibitors of the phosphodiesterase 4 (PDE4) enzyme. More particularly, the invention relates to derivatives of 1-phenyl-2-pyridynyl alkylene alcohols, methods of preparing such compounds, compositions containing them and therapeutic use thereof.

BACKGROUND OF THE INVENTION

Airway obstruction characterizes a number of severe respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, avoiding any systemic side-effects, thus resulting in a more rapid clinical response and a higher therapeutic ratio.

Inhaled corticosteroids are the current maintenance therapy of choice for asthma and together with bronchodilator beta2-agonists for acute symptom relief, they form the mainstay of current therapy for the disease. The current management of COPD is largely symptomatic by means of bronchodilating therapy with inhaled anticholinergics and inhaled beta2-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated.

It has been found that PDE4 exists in two distinct forms representing different conformations, that were designated as high affinity rolipram binding site or HPDE4, especially present in the central nervous system and in parietal cells, and low affinity rolipram binding site or LPDE4 (Jacobitz, S et al Mol. Pharmacol, 1996, 50, 891-899), which is found in the immune and inflammatory cells. While both forms appear to exhibit catalytic activity, they differ with respect to their sensitivity to inhibitors. In particular compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as cilomilast and roflumilast. However, even these compounds are not provided with a good selectivity towards LPDE4.

Other classes of compounds acting as PDE4 inhibitors have been disclosed in the prior art.

For example, WO 9402465 discloses, inter alia, ketone derivatives of general formula

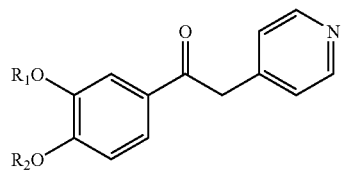

wherein $R_1$ is lower alkyl, and $R_2$ may be alkyl, alkenyl, cycloalkyl, cycloalkyl, cycloalkenyl, cyclothioalkyl or cyclothioalkenyl.

WO 9535281 in the name of Celltech Therapeutics concerns tri-substituted phenyl derivatives generically belonging to the classes of ethers and enol ethers. However only ethers derivatives are exemplified.

Both applications are silent about the problems of the side effects associated with inhibition of HPDE4 and do not report data regarding affinity toward HPDE4 and LPDE4.

Therefore, although several PDE4 inhibitors have been disclosed so far, there is still a need for more efficacious and better tolerated compounds.

In particular it would be highly advantageous to provide more selective compounds, e.g. endowed with a higher affinity toward the LPDE4 in comparison to HPDE4, in order to attenuate or avoid the side effects associated with its inhibition.

The present invention addresses these issues by providing PDE4 inhibitors having an improved selectivity toward LPDE4. While the PDE4 inhibitors of the prior art described above are provided with only two moieties able to interact with the active site of PDE4, the inhibitors of the present invention are characterized by an additional moiety. Said additional moiety is able to further interact with the active site of the PDE4, thereby improving the selectivity of the inhibitors towards LPDE4.

The PDE4 inhibitors of the present invention have been shown to efficaciously act upon inhalation administration and to be characterized by a good persistency in the lung and a short systemic duration.

SUMMARY OF THE INVENTION

The invention is directed to compounds acting as inhibitors of the phosphodiesterase 4 (PDE4) enzyme, methods of preparing such compounds, compositions containing them and therapeutic use thereof.

In particular the invention is directed to derivatives of 1-phenyl-2-pyridynyl alkylene alcohols of general formula (I)

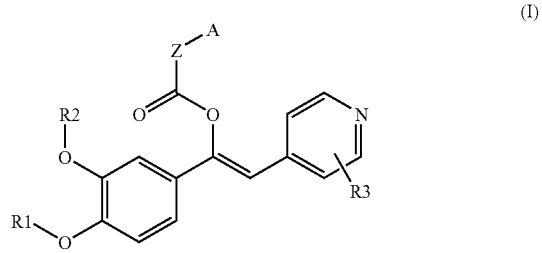

wherein:

Z is selected from the group consisting of $(CH_2)_n$ wherein n=0.1, or 2;

$O(CH_2)_m$ wherein m=1, 2 or 3;

$(CH_2)_pO$ wherein p is 1, 2 or 3;

$CH_2SO_2$;

$CH_2NR_6$ or $NR_6$ wherein $R_6$ is H or a linear or branched $C_1$-$C_6$ alkyl;

$CR_4R_5$ wherein $R_4$ is independently selected from the group consisting of H or a linear or branched $C_1$-$C_4$ alkyl, preferably methyl, and $R_5$ is independently selected from the group consisting of linear or branched $C_1$-$C_4$ alkyl;

phenyl;

benzyl;

$NH_2$;

HNCOOR' wherein R' is linear or branched $C_1$-$C_4$ alkyl, preferably t-butyl;

otherwise when $R_4$ and $R_5$ are both linear or branched $C_1$-$C_4$ alkyl they form a ring with the carbon atom they are linked to having 3, 4, 5 or 6 carbon atoms, preferably having 3 carbon atoms;

$R_1$ and $R_2$ are the same or different and are independently selected from the group consisting of

H;

linear or branched $C_1$-$C_6$ alkyl, unsubstituted or substituted by one or more substituents selected from the group consisting of $C_3$-$C_7$ cycloalkyl or $C_3$-$C_7$ cycloalkenyl;

$C_3$-$C_7$ cycloalkyl;

$C_5$-$C_7$ cycloalkenyl;

linear or branched $C_2$-$C_6$ alkenyl; and linear or branched $C_2$-$C_6$ alkynyl.

$R_3$ is one or more substituents independently selected from the group consisting of H, cyano, nitro, $CF_3$ or halogen atoms;

A is an optionally substituted ring system in which the optional substituent $R_x$ can be one or more, may be the same or different, and is independently selected from the group consisting of:

linear or branched $C_1$-$C_6$ alkyl, optionally substituted with one or more with one or more substituents selected form the group consisting of $C_3$-$C_7$ cycloalkyl and $C_5$-$C_7$ cycloalkenyl;

linear or branched $C_2$-$C_6$ alkenyl;

linear or branched $C_2$-$C_6$ alkynyl;

$C_3$-$C_7$ cycloalkyl;

$C_5$-$C_7$ cycloalkenyl;

$OR_7$ wherein $R_7$ is selected from the group consisting of H, linear or branched $C_1$-$C_6$ alkyl wherein the $C_1$-$C_6$ alkyl group can be unsubstituted or substituted by one or more substituents selected from the group consisting of $C_3$-$C_7$ cycloalkyl; phenyl, benzyl or $NR_8R_9$—$C_1$-$C_4$ alkyl wherein $R_8$ and $R_9$ are the same or different and are independently selected from the group consisting of H, linear or branched $C_1$-$C_6$ or they form with the nitrogen atom to which are linked a saturated or partially saturated cycloalkyl ring, preferably a piperidyl ring;

halogen atoms;

cyano;

$NR_{10}R_{11}$ wherein $R_{10}$ and $R_{11}$ are the same or different and are independently selected from the group consisting of H, linear or branched $C_1$-$C_6$, $COC_6H_5$ and $COC_1$-$C_4$ alkyl, or they form with the nitrogen atom to which are linked a saturated or partially saturated cycloalkyl ring, preferably a piperidyl ring oxo;

$HNSO_2R_{12}$ wherein $R_{12}$ is $C_1$-$C_6$ alkyl or a phenyl optionally substituted with halogen atoms or with a $C_1$-$C_4$ alkyl group;

$SO_2R_{13}$ wherein $R_{13}$ is OH, $C_1$-$C_4$ alkyl or $NR_{10}R_{11}$ wherein $R_{10}$ and $R_{11}$ are as define above;

$SR_{14}$ wherein $R_{14}$ is H, phenyl or $C_1$-$C_4$alkyl;

$SOR_{15}$ wherein $R_{14}$ is phenyl or $C_1$-$C_4$ alkyl;

$COOR_{16}$ wherein $R_{16}$ is H or $C_1$-$C_4$ alkyl, phenyl or benzyl;

$(CH_2)_qOR_{17}$. wherein p=1, 2, 3 or 4 and $R_{17}$ is H or $C_1$-$C_4$ alkyl, phenyl benzyl or $COC_1$-$C_4$ alkyl; and $COR_{18}$ wherein $R_{18}$ is phenyl or $C_1$-$C_6$ alkyl.

The invention also includes the corresponding N-oxides on the pyridine ring.

The invention further encompasses pharmaceutically acceptable salts and/or solvates thereof.

The present invention also provides pharmaceutical compositions of compounds of general formula (I) alone or in admixture with one or more pharmaceutically acceptable carriers.

In a further aspect the present invention provides the use of a compound of general formula (I) for the preparation of a medicament for the prevention and/or treatment of any disease wherein PDE4 inhibition is required.

In particular the compounds of general formula (I) alone or combined with other active ingredients may be administered for the prevention and/or treatment of a disease of the respiratory tract characterized by airway obstruction such as asthma and COPD.

Moreover the present invention provides a method for the prevention and/or treatment of any disease wherein PDE4 inhibition is required, said method comprises administering to a patient in need of such treatment a therapeutically effective amount of a compound of general formula (I).

Definitions

The term "halogen atoms" as used herein includes fluorine, chlorine, bromine, and iodine.

As used herein, the expression "linear or branched $C_1$-$C_x$ alkyl" where x is an integer greater than 1, refers to straight and branched chain alkyl groups wherein the number of constituent carbon atoms is in the range 1 to x. Particular alkyl groups are methyl, ethyl, n-propyl, isopropyl and t-butyl.

Optionally in said groups one or more hydrogen atoms can be replaced by a halogen atom, preferably chlorine or fluorine.

The derived expressions "$C_2$-$C_6$ alkenyl" and "$C_2$-$C_6$ alkynyl", are to be construed in an analogous manner.

As used herein, the expression "$C_3$-$C_x$ cycloalkyl", where x is an integer greater than 3, refers to cyclic non-aromatic hydrocarbon groups containing from 3 to x ring carbon atoms. Examples include cyclopropyl, cyclobutyl, cyclopentyl, cyclohexyl and cycloheptyl. Optionally in said groups one or more hydrogen atoms can be replaced by fluorine atoms.

The derived expression "$C_5$-$C_x$ cycloalkenyl", where x is an integer greater than 5, is to be construed in an analogous manner.

As used herein, the expression "ring system" refers to mono- or bicyclic ring systems which may be saturated, partially unsaturated or unsaturated, such as aryl, $C_3$-$C_8$ cycloalkyl or heteroaryl, having 5 to 10 ring atoms in which at least 1 ring atom is a heteroatom (e.g. N, S or O).

Examples of suitable monocyclic systems include phenyl, pyridyl, piperazinyl, piperidinyl, morpholinyl, cyclopentyl, cyclohexyl, cyclohexenyl and cycloheptyl. Examples of suitable bicyclic systems include naphthyl, quinolinyl, isoquinolinyl, indenyl and the partially- or fully-hydrogenated derivatives thereof.

DETAILED DESCRIPTION OF THE INVENTION

The invention is directed to compounds acting as inhibitors of the phosphodiesterase 4 (PDE4) enzyme.

Said class of compounds inhibit the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3, and tumor necrosis factor-alpha (TNF-α).

It also lead to an airway smooth muscle relaxation and a decrease in oedema.

The catalytic site of PDE4 has been identified: it mainly comprises a hydrophobic region in which two sub-pockets are present, e.g. $S_o$ and $S_1$, and a hydrophilic region containing the metal ions $Zn^{2+}$ and $Mg^{2+}$, that in turn comprises the sub-pocket $S_2$ spreading around the metal ions and a sub-pocket $S_3$ which branches approximately 90° from the middle of the hydrophobic pocket.

Most of the compounds of the prior art are provided with a moiety able of interacting with the sub-pockets $S_0$ and $S_1$ of the hydrophobic region such as a substituted catechol group and with another moiety able of indirectly interacting with the metal ions of the $S_2$ sub-pocket, for example a heterocycle such as pyridine or pyrrolidone.

The present invention is directed to compounds which were designed so that they could maintain the interactions with the sub-pockets $S_o$ and $S_1$ by means of the substituted catechol moiety and the interaction with the metal ions region by means of the pyridine ring like other known PDE4 inhibitors but differ for the presence of a further group able of establishing an additional interaction with the sub-pocket $S_3$.

In particular the present invention relates to derivatives of 1-phenyl-2-pyridynyl alkylene alcohols of general formula (I)

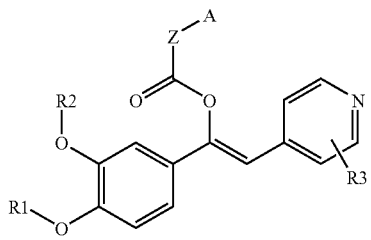

(I)

wherein:

Z is selected from the group consisting of
(CH$_2$)$_n$ wherein n=0.1, or 2;
O(CH$_2$)$_m$ wherein m=1, 2 or 3;
(CH$_2$)$_p$O wherein p is 1, 2 or 3;
CH$_2$SO$_2$;
CH$_2$NR$_6$ or NR$_6$ wherein R$_6$ is H or a linear or branched C$_1$-C$_6$ alkyl;
CR$_4$R$_5$ wherein R$_4$ is independently selected from the group consisting of H or a linear or branched C$_1$-C$_4$ alkyl, preferably methyl, and R$_5$ is independently selected from the group consisting of linear or branched C$_1$-C$_4$ alkyl;
phenyl;
benzyl;
NH$_2$;
HNCOOR' wherein R' is linear or branched C$_1$-C$_4$ alkyl, preferably t-butyl;
otherwise when R$_4$ and R$_5$ are both linear or branched C$_1$-C$_4$ alkyl they form a ring with the carbon atom they are linked to having 3, 4, 5 or 6 carbon atoms, preferably having 3 carbon atoms;

R$_1$ and R$_2$ are the same or different and are independently selected from the group consisting of
H;
linear or branched C$_1$-C$_6$ alkyl, optionally substituted with one or more substituents selected form the group consisting of C$_3$-C$_7$ cycloalkyl and C$_5$-C$_7$ cycloalkenyl;
linear or branched C$_2$-C$_6$ alkenyl;
linear or branched C$_2$-C$_6$ alkynyl;
C$_3$-C$_7$ cycloalkyl; and
C$_5$-C$_7$ cycloalkenyl;

R$_3$ is one or more substituents independently selected from the group consisting of H, cyano, nitro, CF$_3$ or halogen atoms;

A is an optionally substituted ring system in which the optional substituent R$_x$ can be one or more, may be the same or different, and is independently selected from the group consisting of:
linear or branched C$_1$-C$_6$ alkyl, optionally substituted with one or more with one or more substituents selected form the group consisting of C$_3$-C$_7$ cycloalkyl and C$_5$-C$_7$ cycloalkenyl;
linear or branched C$_2$-C$_6$ alkenyl;
linear or branched C$_2$-C$_6$ alkynyl;
C$_3$-C$_7$ cycloalkyl;
C$_5$-C$_7$ cycloalkenyl;
OR$_7$ wherein R$_7$ is selected from the group consisting of H, linear or branched C$_1$-C$_6$ alkyl wherein the C$_1$-C$_6$ alkyl group can be unsubstituted or substituted by one or more substituents selected from the group consisting of C$_3$-C$_7$ cycloalkyl; phenyl, benzyl or NR$_8$R$_9$—C$_1$-C$_4$ alkyl wherein R$_8$ and R$_9$ are the same or different and are independently selected from the group consisting of H, linear or branched C$_1$-C$_6$ or they form with the nitrogen atom to which are linked a saturated or partially saturated cycloalkyl ring, preferably a piperidyl ring;
halogen atoms;
cyano;
NR$_{10}$R$_{11}$ wherein R$_{10}$ and R$_{11}$ are the same or different and are independently selected from the group consisting of H, linear or branched C$_1$-C$_6$, COC$_6$H$_5$ and COC$_1$-C$_4$ alkyl, or they form with the nitrogen atom to which are linked a saturated or partially saturated cycloalkyl ring, preferably a piperidyl ring;
oxo;
HNSO$_2$R$_{12}$ wherein R$_{12}$ is C$_1$-C$_6$ alkyl or a phenyl optionally substituted with halogen atoms or with a C$_1$-C$_4$ alkyl group;
SO$_2$R$_{13}$ wherein R$_{13}$ is OH, C$_1$-C$_4$ alkyl or NR$_{10}$R$_{11}$ wherein R$_{10}$ and R$_{11}$ are as define above;
SR$_{14}$ wherein R$_{14}$ is H, phenyl or C$_1$-C$_4$ alkyl;
SOR$_{15}$ wherein R$_{14}$ is phenyl or C$_1$-C$_4$ alkyl;
COOR$_{16}$ wherein R$_{16}$ is H or C$_1$-C$_4$ alkyl, phenyl or benzyl;
(CH$_2$)$_q$OR$_{17}$ wherein p=1, 2, 3 or 4 and R$_{17}$ is H or C$_1$-C$_4$ alkyl, phenyl benzyl or COC$_1$-C$_4$ alkyl; and $COR_{18}$ wherein $R_{18}$ is phenyl or $C_1$-$C_6$ alkyl.

The invention also includes the corresponding N-oxides on the pyridine ring.

Moreover it encompasses pharmaceutically acceptable salts and/o solvates thereof.

Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid.

Pharmaceutically acceptable salts also include those in which acidic functions, when present, are reacted with an appropriate base to form, e.g. sodium, potassium, calcium, magnesium, ammonium, and choline salts.

It will be apparent to those skilled in the art that the compounds of general formula (I) may exhibit geometrical isomerism and may contain asymmetric centers.

Therefore the invention includes both the E- and Z geometric isomers on the double bond (cis and trans forms) and also the optical stereoisomers and mixtures thereof.

Preferably the substituents on the double bond in compounds of general formula (I) are arranged in the trans conformation (Z-isomers).

The compounds of general formula (I) were found to show an in vitro inhibitory activity toward the PDE4 enzyme in the nM range and they turned out to be endowed of a good activity in the lungs upon intra-tracheal administration in an animal model of COPD.

They also exhibited sustained pulmonary levels in the lungs, while no detectable plasmatic levels were found which an index of a short systemic action.

Moreover it has been found that the additional interaction with the sub-pocket $S_3$ of the catalytic site of the PDE4 enzyme through the A substituent is able of assuring a higher selectivity toward LPDE4 in comparison to HPDE4.

As it can be appreciated from the results reported in the Example 39, a compound representative of the invention was indeed found about 58-fold more selective toward LPDE4 versus HPDE4, whereas the corresponding ketone, e.g. a compound lacking of the A substituent, turned out to inhibit LPDE4 and HPDE4 forms with similar potency.

A preferred group of compounds of general formula (I) is that wherein the pyridine ring is substituted in 3 and 5 with two chlorine atoms, according to the general formula (II).

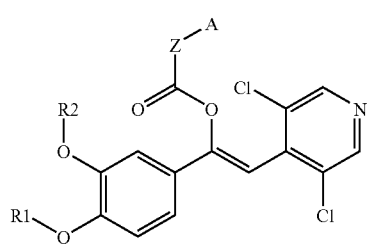

(II)

wherein $R_1$, $R_2$, and Z are as defined above, and

A is a ring system selected from phenyl ring or a heteroaryl ring unsaturated or partially unsaturated, having 5 to 10 ring atoms in which at least 1 ring atom is a heteroatom (e.g. N, S or O), optionally substituted as defined above.

Advantageously when $R_1$ or $R_2$ is H, the other subsistent of the catechol group is different from H.

In a preferred embodiment $R_1$ and $R_2$ are both different from H.

A first group of more preferred compounds of general formula (II) is that in which:
$R_1$ and $R_2$ are as defined above;
Z is $(CH_2)_n$ wherein n is 0; and
A is optionally substituted phenyl as defined above.

A second group of more preferred compounds is that in which:
$R_1$ and $R_2$ are as defined above;
Z is $CHR_5$ wherein $R_5$ is linear or branched $C_1$-$C_4$ alkyl, preferably methyl; and
A is optionally substituted phenyl as defined above.

A third group of more preferred compounds is that in which:
$R_1$ and $R_2$ are as defined above;
Z is $CR_4R_5$ wherein $R_4$ and $R_5$ are both linear or branched $C_1$-$C_4$ alkyl and they form a ring with the carbon atom they are linked to having 3, 4, 5 or 6 carbon atoms, preferably having 3 carbon atoms; and
A is optionally substituted phenyl as defined above.

A fourth group of preferred compounds is that in which:
$R_1$ and $R_2$ are as defined above;
Z is $(CH_2)_n$ wherein n is 0; and
A is optionally substituted heteroaryl as defined above.

A fifth group of preferred compounds is that in which:
$R_1$ and $R_2$ are as defined above;
Z is $CHR_5$ wherein $R_5$ is linear or branched $C_1$-$C_4$ alkyl, preferably methyl; and
A is optionally substituted heteroaryl as defined above.

A sixth group of preferred compounds is that in which:
$R_1$ and $R_2$ are as defined above;
Z is $CR_4R_5$ wherein $R_4$ and $R_5$ are both linear or branched $C_1$-$C_4$ alkyl and they form a ring with the carbon atom they are linked to having 3, 4, 5 or 6 carbon atoms, preferably having 3 carbon atoms; and
A is optionally substituted heteroaryl as defined above.

In one of the preferred embodiment the optional subsistent $R_x$ is selected from the group consisting of linear or branched $C_1$-$C_6$ alkyl, linear or branched $C_2$-$C_6$ alkenyl, linear or branched $C_2$-$C_6$ alkynyl. or $OR_7$ wherein $R_7$ is as defined above.

In another preferred embodiment $R_x$ is a group able of improving the aqueous solubility of the whole molecule such as $NR_{10}R_{11}$ or $HNSO_2R_{12}$ wherein $R_{10}$, $R_{11}$ and $R_{12}$ are as defined above.

In a particular embodiment of the invention, when A is a heteroaryl ring, the ring is preferably selected from the group consisting of pyrrole, pyrazole, furan, thiophene, imidazole, oxazole, isoxazole, thiazole, pyridine, pyrimidine, pyrazine, pyridazine, and pyran, more preferably pyridine.

In a further aspect the present invention provides the following compounds:

| Internal code | Chemical name |
|---|---|
| CHF 5405 | 3,4-Dimethoxy-benzoic acid, (Z)-2-(3,5-dichloro-pyridin-4-yl)-1-(3,4-dimethoxy-phenyl)- vinyl ester |

-continued

| Internal code | Chemical name |
| --- | --- |
| CHF 5408 | 3-Cyclopentyloxy-4-methoxy-benzoic acid, (Z)-1-(3-cyclopentyloxy-4-methoxy-phenyl)-2-(3,5-dichloro-pyridin-4-yl)vinyl ester |
| CHF 5415 | Benzoic acid, (Z)-2-(3,5-dichloro-pyridin-4-yl)-1-(3,4-dimethoxy-phenyl)vinyl ester |
| CHF 5429 | 4-Methoxy-benzoic acid, (Z)-2-(3,5-dichloro-pyridin-4-yl)-1-(3,4-dimethoxy-phenyl)vinyl ester |
| CHF 5472 | 3,4-Dimethoxy-benzoic acid, (Z)-1-(3-cyclopropylmethoxy-4-difluoromethoxy-phenyl)-2-(3,5-dichloro-pyridin-4-yl)vinyl ester |
| CHF 5480 | 2-(S)-(4-Isobutyl-phenyl)-propionic acid, (Z)- 2-(3,5-dichloro-pyridin-4-yl)-1-(3,4-dimethoxy-phenyl)vinyl ester |
| CHF 5513 | 4-Nitro-benzoic acid, (Z)- 2-(3,5-dichloro-pyridin-4-yl)-1-(3,4-dimethoxy-phenyl)vinyl ester |
| CHF 5514 | 3-Cyclopropylmethoxy-4-difluoromethoxy-benzoic acid, (Z)-1-(3-cyclopropylmethoxy-4-difluoromethoxy-phenyl)-2-(3,5-dichloro-pyridin-4-yl)vinyl ester |
| CHF 5517 | 3-Difluoromethoxy-4-Cyclopentyloxy-benzoic acid, (Z)-1-(4-cyclopentyloxy-3-difluoromethoxy-phenyl)-2-(3,5-dichloro-pyridin-4-yl)vinyl ester |
| CHF 5522 | (3,4-Dimethoxy-phenyl)-carbamic acid, (Z)-1-(3-cyclopropylmethoxy-4-difluoromethoxy-phenyl)-2-(3,5-dichloro-pyridin-4-yl)vinyl ester |
| CHF 5524 | 3-Benzyloxy-benzoic acid (Z)-2-(3,5-dichloro-pyridin-4-yl)-1-(3,4-dimethoxy-phenyl)vinyl ester |
| CHF 5526 | 4-Methanesulfonylamino-benzoic acid (Z)-2-(3,5-dichloro-pyridin-4-yl)-1-(3,4-dimethoxy-phenyl)vinyl ester |
| CHF 5528 | 3-Benzyloxy-4-methoxy-benzoic acid, (Z)-1-(3-cyclopentyloxy-4-methoxy-phenyl)-2-(3,5-dichloro-pyridin-4-yl)vinyl ester |
| CHF 5530 | 4-Amino-benzoic acid, (Z)-2-(3,5-dichloro-pyridin-4-yl)-1-(3,4-dimethoxy-phenyl)vinyl ester |
| CHF 5532 | 3,4-Dimethoxy-benzoic acid, (Z)-1-(3-cyclopentyloxy-4-methoxy-phenyl)-2-(3,5-dichloro-pyridin-4-yl)vinyl ester |
| CHF 5533 | 4-(4-Fluoro-benzenesulfonylamino)-benzoic acid, (Z)-2-(3,5-dichloro-pyridin-4-yl)-1-(3,4-dimethoxy-phenyl)vinyl ester |
| CHF 5537 | 4-(Toluene-4-sulfonylamino)-benzoic acid, (Z)-2-(3,5-dichloro-pyridin-4-yl)-1-(3,4-dimethoxy-phenyl)vinyl ester |
| CHF 5538 | 2-(4-Isobutyl-phenyl)-propionic acid, (Z)-1-(3-cyclopentyloxy-4-methoxy-phenyl)-2-(3,5-dichloro-pyridin-4-yl)vinyl ester |
| CHF 5543 | 2-(S)-(4-Isobutyl-phenyl)-propionic acid, (E)-1-(3-cyclopentyloxy-4-methoxy-phenyl)-2-(3,5-dichloro-pyridin-4-yl)vinyl ester |
| CHF 5542 | 3-Benzyloxy-4-methoxy-benzoic acid, (Z)-2-(3,5-dichloro-pyridin-4-yl)-1-(3,4-dimethoxy-phenyl)vinyl ester |
| CHF 5546 | 3-Cyclopropylmethoxy-4-methoxy-benzoic acid, (Z)-1-(3-cyclopropylmethoxy-4-methoxy-phenyl)-2-(3,5-dichloro-pyridin-4-yl)vinyl ester |
| CHF 5550 | Methyl-o-tolyl-carbamic acid, (Z)- 2-(3,5-dichloro-pyridin-4-yl)-1-(3,4-dimethoxy-phenyl)vinyl ester |
| CHF 5555 | 3-Cyclopropylmethoxy-4-difluoromethoxy-benzoic acid, (Z)-2-(3,5-dichloro-pyridin-4-yl)-1-(3,4-dimethoxy-phenyl)vinyl ester |
| CHF 5557 | 1-p-Tolyl-cyclopropanecarboxylic acid, (Z)-2-(3,5-dichloro-pyridin-4-yl)-1-(3,4-dimethoxy-phenyl)vinyl ester |
| CHF 5558 | Phenyl-acetic acid, (Z)-2-(3,5-dichloro-pyridin-4-yl)-1-(3,4-dimethoxy-phenyl)vinyl ester |
| CHF 5559 | 2-(R)-phenyl-propionic acid, (Z)- 2-(3,5-dichloro-pyridin-4-yl)-1-(3,4-dimethoxy-phenyl)vinyl ester |
| CHF 5574 | Methyl-phenyl-carbamic acid, (Z)- 2-(3,5-dichloro-pyridin-4-yl)-1-(3,4-dimethoxy-phenyl)vinyl ester |
| CHF 5605 | Phenyl-acetic acid, (Z)- 1-(3-cyclopentyloxy-4-methoxy-phenyl)-2-(3,5-dichloro-pyridin-4-yl)vinyl ester |
| CHF 5606 | 3,4-Dimethoxy-benzoic acid, (Z)- 1-(3-cyclopropylmethoxy-4-methoxy-phenyl)-2-(3,5-dichloro-pyridin-4-yl)vinyl ester |
| CHF 5613 | 4-(2-Piperidin-1-yl-ethoxy)-benzoic acid 2-(3,5-dichloro-pyridin-4-yl)-1-(3,4-dimethoxy-phenyl)vinyl ester |
| CHF 5614 | 3,4-Dimethoxy-benzoic acid 2-(3,5-dichloro-1-oxy-pyridin-4-yl)-1-(3,4-dimethoxy-phenyl)vinyl ester |
| CHF 5622 | 3,4-Bis-difluoromethoxy-benzoic acid 1-(3,4-bis-difluoromethoxy-phenyl)-2-(3,5-dichloro-pyridin-4-yl)vinyl ester |
| CHF 5623 | 2-(S)-Phenyl-propionic acid, (Z)-2-(3,5-dichloro-pyridin-4-yl)-1-(3,4-dimethoxy-phenyl)vinyl ester |
| CHF 5625 | 2-(4-Isobutyl-phenyl)-propionic acid 1-(3-cyclopropylmethoxy-4-methoxy-phenyl)-2-(3,5-dichloro-pyridin-4-yl)vinyl ester |
| CHF 5626 | Phenyl-carbamic acid 2-(3,5-dichloro-pyridin-4-yl)-1-(3,4-dimethoxy-penyl)vinyl ester |
| CHF 5636 | 4-Oxo-4H-pyran-2-carboxylic acid 2-(3,5-dichloro-pyridin-4-yl)-1-(3,4-dimethoxy-phenyl)vinyl ester |
| CHF 5637 | Benzyl-carbamic acid 2-(3,5-dichloro-pyridin-4-yl)-1-(3,4-dimethoxy-phenyl)vinyl ester |
| CHF 5638 | 2-(S)-(4-Isobutyl-phenyl)-propionic acid 1-(3-cyclopropylmethoxy-4-difluoromethoxy-phenyl)-2-(3,5-dichloro-pyridin-4-yl)vinyl ester |

-continued

| Internal code | Chemical name |
|---|---|
| CHF 5642 | 3-Cyclopentyloxy-4-methoxy-benzoic acid 2-(3,5-dichloro-pyridin-4-yl)-1-(3,4-dimethoxy-phenyl)vinyl ester |
| CHF 5643 | 3-Cyclopentyloxy-4-methoxy-benzoic acid 1-(3-cyclopentyloxy-4-methoxy-phenyl)-2-(3,5-dichloro-1-oxy-pyridin-4-yl)vinyl ester |
| CHF 5647 | (4-Isopropyl-phenyl)-carbamic acid 2-(3,5-dichloro-pyridin-4-yl)-1-(3,4-dimethoxy-phenyl)vinyl ester |
| CHF 5649 | 3-Cyclopropylmethoxy-4-difluoromethoxy-benzoicacid-1-(3-cyclopropylmethoxy-4-difluoromethoxy-phenyl)-2-(3,5-dichloro-1-oxy-pyridin-4-yl)vinyl ester |
| CHF 5656 | 2-(S)-(4-Isobutyl-phenyl)-propionic acid (E)-2-(3,5-dichloro-pyridin-4-yl)-1-(3,4-dimethoxy-phenyl)vinyl ester |

Advantageously the compounds of the invention are characterized by a selectivity toward LPDE4 higher than that toward HPDE4 as obtained by the determination of their $IC_{50}$.

In the case of LPDE4, the $IC_{50}$ is the molar concentration of the test compound producing 50% inhibition of cAMP disappearance, assessed as described in Cortijo J et al *Br J Pharmacol* 1993, 108: 562-568, while in the case of HPDE4, the $IC_{50}$ is the molar concentration of the test compound producing 50% inhibition of the binding of $[H^3]$rolipram, assessed as described in Duplantier A J et al *J Med Chem* 1996; 39: 120-125.

Preferably the HPDE4/LPDE4 $IC_{50}$ ratio for the compounds of the invention is higher than 10, more preferably higher than 20, even more preferably higher than 50.

The compounds of general formula (I) may be prepared conventionally according to methods disclosed in the art. Some of the processes which can be used are described below and reported in Scheme 1 and should not be viewed as limiting the scope of the synthetic methods available for the preparation of the compounds of the invention.

According to a first embodiment of the present invention (Method A, scheme 1) the compounds of general formula (I) are prepared according to a process which includes the following steps:

1$^{st}$ step—reaction of an acyl chloride of formula (5) wherein $R_1$ and $R_2$ are as defined above with a 4-methylpyridine of formula (6) wherein $R_3$ is as defined above to give an ethanone derivative of general formula (7).

The reaction may be carried out by activation of the methyl group of a compound of formula (6) by means of an equimolar amount or a slight excess of a strong base such as NaH, lithium diisopropylamide (LDA), dimethylaminopyridine (DMAP) in an aprotic solvent such as tetrahydrofuran (THF) dimethylformamide (DMF), ethyl ether, dioxane, or toluene at a temperature comprised between −80° and room temperature and subsequent addition of an acyl chloride of general formula (5), also maintained at a temperature comprised between −80° C. to room temperature, preferably between −80° and −20° C.

The medium reaction is maintained at a temperature comprised between −80° and room temperature, preferably between −80° and −20° C., and quenched with water maintained at the same temperature to obtain the ethanone of formula (7).

2$^{nd}$ step—isolation of the obtained ethanone by means of conventional procedures such as filtration.

3rd step—reaction of the ethanone of step 2) with a strong base such as NaH, LDA, DMAP in an aprotic solvent such as THF, DMF, ethyl ether, dioxane, toluene at a temperature comprised between −80° and −20° C. to obtain the corresponding reactive enolate, followed by addition of a suitable acyl chloride AZCOCl an equimolar ratio or in a slight excess, wherein A and Z are as defined above, at a temperature comprised between −80° and room temperature, to obtain the final product.

Alternatively a suitable isocyanate AZNCO or a suitable carboxylic acid AZCOOH (in presence of condensing agents such as a carbodiimide and N-hydroxybenzotriazole) may be used according to conventional methods.

The compounds of general formula (I) may also be prepared in a single step without isolation of the intermediate ethanone of formula (7).

Said reaction, which is reported in the Scheme 1 as method B, is carried out by activation of the methyl group of a compound of general formula (6) by means of an excess (2 to 6 fold excess, preferably 2 to 3 fold excess) of an appropriate strong base such as LDA, NaH, DMAP in an aprotic solvent such as THF, DMF, ethyl ether, dioxane, toluene, at a temperature comprised between −80° and −20° C., and subsequent addition of a suitable acyl chloride AZCOCl maintained at a temperature comprised between −80° C. and −20° C., preferably between −80° C. and −60° C. in an equimolar ratio with the compound of formula (6).

The temperature of the reaction medium is maintained between −80° and −20°, then a suitable acyl chloride AZCOCl in an equimolar ratio, or in an slight excess, is added. The temperature of the reaction medium is gradually left to rise to room temperature to obtain the final compound.

Alternatively, a suitable isocyanate AZNCO or a suitable carboxylic acid AZCOOH (in presence of condensing agents such as a carbodiimide and N-hydroxybenzotriazole) may be used according to conventional methods.

For obtaining "symmetric" derivatives, e.g. the compounds of general formula (I) wherein Z is $(CH_2)_n$ with n=0 and A is a 3,4 dihydroxy phenyl derivative wherein the oxygen atoms are substituted with $R_1$ and $R_2$ groups as defined above, the process may be carried by simply reacting the 4-methylpyridine of formula (6) with a strong base (twice molar ratio or a slight excess) in an aprotic solvent, at a temperature between −80° C. and room temperature, then with the acyl chloride derivative of formula (5) in a twice molar ratio or a slight excess.

The compounds of formula (5) may be prepared starting from the compound of formula (1) according to conventional methods.

The compound of formula (1) is commercially available.

The compounds of formula (6) are commercially available or may be prepared according to conventional methods. For example, the preparation of the 3,5-dichloro-4-methylpyridine is reported in WO 94/14742.

The N-oxides on the pyridine ring of compounds of general formula (I) may be obtained according to conventional methods. For instance they may be prepared by dissolving a compound of general formula (I) in a chlorinated solvent such as $CH_2Cl_2$ or $CHCl_3$ then adding m-chloro perbenzoic acid (mCPBA) to the resulting solution.

Scheme 1

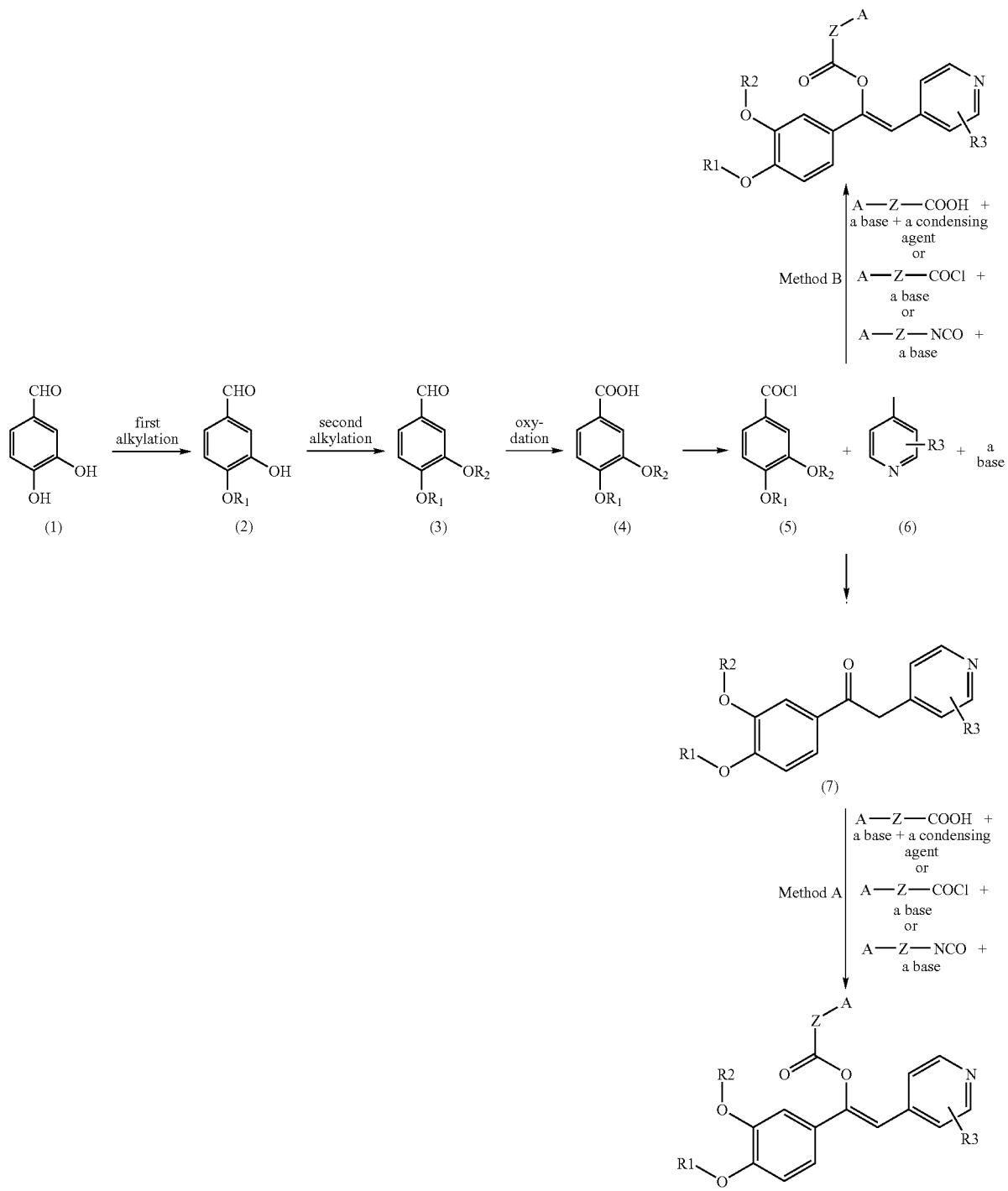

The present invention also provides pharmaceutical compositions of compounds of general formula (I).

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized, wherein the powder can be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction can be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination with other pharmaceutical active ingredients including those currently used in the treatment of respiratory disorders, e.g. beta2-agonists such as salbutamol, formoterol, salmeterol and carmoterol (TA 2005), corticosteroids such as budesonide and its epimers, beclometasone dipropionate, triamcinolone acetonide, fluticasone propionate, flunisolide, mometasone furoate, rofleponide and ciclesonide and anticholinergic or antimuscarinic agents such as ipratropium bromide, oxytropium bromide, tiotropium bromide, glycopyrrolate bromide, revatropate or the compounds disclosed in WO 03/053966.

Preferably the compounds of general formula (I) alone or combined with other active ingredients may be administered for the prevention and/or treatment of a disease the respiratory tract characterized by airway obstruction such as asthma, chronic bronchitis, chronic obstructive pulmonary disease (COPD).

However the compounds of general formula (I) may be used for the prevention and/or treatment any disease wherein PDE4 inhibition is required.

Said diseases include allergic and inflammatory disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular and wide-area pyodermias, endogenous and exogenous acne, acne rosacea, Behcet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, they are administered at a dosage comprised between 0.01 and 1000 mg/day, preferably between 0.1 and 500 mg/day.

When given by inhalation route, the compounds of the invention may be administered for example, at a dosage comprised between 0.01 and 10 mg/day, preferably between 0.05 and 5 mg/day, more preferably between 0.1 and 2 mg/day.

The present invention will now be further described by way of the following non-limiting examples.

EXAMPLES

Preparation of the Intermediates of Formula (2), (3), (4), (5), (6) and (7) of Scheme 1

Example 1

Preparation of 4-difluoromethoxy-3-hydroxybenzaldehyde (2)

A solution of 3,4-dihydroxybenzaldehyde (16.6 g, 120 mmol) and sodium chlorodifluoroacetate (18.3 g, 120 mmol) in dimethylformamide (150 ml) and water (3 ml) was added with sodium hydroxide (4.8 g, 120 mmol), heated to 120° C. and stirred at this temperature for 2 hrs. The solvent was removed by vacuum distillation and the residue added with aqueous hydrochloric acid (20 ml). The mixture was extracted with diethyl ether (2×50 ml), the combined organic layers were washed with water and brine and the solvent removed under reduced pressure. The crude product was purified by chromatography on silica gel (hexane/ethyl acetate 8:2) to furnish 4-difluoromethoxy-3-hydroxybenzaldehyde as a colourless solid (10 g, 52.8 mmol, 44% yield).

Example 2

Preparation of 3-cyclopropylmethoxy-4-difluoromethoxybenzaldehyde (3)

4-Difluoromethoxy-3-hydroxybenzaldehyde (10 g, 52.8 mmol) was dissolved in tetrahydrofuran (100 ml) added with potassium carbonate (44 g, 105 mmol), cooled to 0° C. and added with a solution of bromomethylcyclopropane (11 ml, 116.6 mmol) in tetrahydrofuran (50 ml). The reaction mixture was heated to reflux under stirring for 7 hrs, then fresh bromomethylcyclopropane (5.5 ml, 58.3 mmol) was added and the heating continued for further 7 hrs. The solvent was removed by vacuum distillation, then the mixture was added with 2 N sodium hydroxide (100 ml) and extracted with dichloromethane (2×100 ml). The combined organic layers were dried over sodium sulphate (5 g) and the solvent removed under reduced pressure to afford 3-cyclopropylmethoxy-4-difluoromethoxybenzaldehyde (12 g, 50 mmol, 97% yield), that was used without further purification.

Example 3

Preparation of 3-cyclopropylmethoxy-4-difluoromethoxybenzoic acid (4)

3-cyclopropylmethoxy-4-difluoromethoxybenzaldehyde (12 g, 50 mmol) and sulfamic acid (7.3 g, 75 mmol) were dissolved in glacial acetic acid (50 ml) and the solution added with a solution of sodium chlorite (8.2 g, 75 mmol) in water (15 ml). The reaction mixture was stirred at room temperature for 1 hr then water (300 ml) was added so obtaining the precipitation of a solid that was filtered and dried at 40° C. under vacuum (12 g, 48 mmol, 97% yield).

Example 4

Preparation of 3-cyclopropylmethoxy-4-difluoromethoxybenzoyl chloride (5)

Thionyl chloride (25 ml, 344 mmol) was added dropwise to a solution of 3-cyclopropylmethoxy-4-difluoromethoxybenzoic acid (12 g, 48 mmol) in toluene (100 ml) and the reaction mixture was heated to reflux for 2 hours, then the solvent was evaporated to dryness under vacuum and the residue was used without further purification (13.2 g, 48 mmol, 100% yield).

Following the teaching of Examples 1-4, other acyl chlorides were prepared starting from the suitable aldehyde derivatives.

Example 5

Preparation of 3,5-dichloro-4-methylpyridine (6)

Diisopropylamine (70 ml, 500 mmol) was dissolved in dry tetrahydrofuran (500 ml), the solution was cooled to −10° C. and butyl lithium (2.5 N in hexane, 210 ml, 525 mmol) was added dropwise under stirring. After 30 minutes the solution was cooled to −20° C. and 3,5-dicholopyridine (66.6 g, 450 mmol) in tetrahydrofuran (200 ml) was added dropwise. The solution was stirred at −10° C. for 30 minutes, cooled to −70° C. and added dropwise with iodomethane (50 ml, 1.6 mol) in tetrahydrofuran (100 ml). The reaction mixture was allowed to warm to room temperature, quenched with water (300 ml) and extracted with diethyl ether (3×100 ml); the combined organic layers were dried over sodium sulphate (5 g) and evaporated to dryness. The crude product was crystallized twice from aqueous ethanol than from hexane to afford 3,5-dichloro-4-methylpyridine (49.9 g, 306 mmol, 68% yield) as a white solid:

MS/ESI+ 162, 164 [MH]+.

Example 6

Preparation of 2-(3,5-dichloro-pyridin-4-yl)-1-(3,4-dimethoxy-phenyl)-ethanone (7)

A solution of 3,5-dichloro-4-methyl-pyridine (2.06 g, 12.7 mmol) in dry tetrahydrofuran (30 ml) was cooled down to −78° C. then a 1.8 M solution of lithium diisopropylamide in tetrahydrofuran (7.4 ml, 13.3 mmol) was added dropwise under stirring, keeping the temperature below −70° C. The resulting solution was stirred for 30 min., then a solution of 3,4-dimethoxy-benzoyl chloride (2.55 g, 12.7 mmol) in dry tetrahydrofuran (20 ml) was added dropwise, maintaining the temperature below −70° C. After stirring for 15 min. ice (20 g) was added, followed by further 500 ml of water. The mixture was extracted with ethyl acetate (2×50 ml), the combined organic layers were dried over sodium sulphate and evaporated under reduced pressure to give an oil that was purified by flash chromatography (Eluent: ethyl acetate/petroleum ether from 10/90 to 30/70 v:v).

2.1 grams (6.4 mmol, 52% yield) of the title compound were obtained as a white solid.

MS/ESI+ 326, 328 [MH]+; $^1$H NMR (CDCl$_3$ calibrated at 7.26 ppm) δ 3.91 and 3.95 (2s, 6H), 4.62 (s, 2H), 6.91-6.95 (d, 1H), 7.53-7.54 (d, 1H), 7.67-7.75 (dd, 1H), 8.49 (s, 2H).

In a similar manner the following ethanone derivatives were prepared:

1-(3-cyclopentyloxy-4-methoxy-phenyl)-2-(3,5-dichloro-pyridin-4-yl)-ethanone (CHF 5400);
1-(3-(cyclopropylmethoxy-4-methoxyphenyl)-2-(3,5-dichloro-4-pyridinyl)-ethanone (CHF 5441);
1-(3-cyclopropylmethoxy-4-difluoromethoxy-phenyl)-2-(3,5-dichloro-pyridin-4-yl)-ethanone (CHF 5471);
1-(3,4-Bis-difluoromethoxy-phenyl)-2-(3,5-dichloro-pyridin-4-yl)-ethanone (CHF 5632);
1-(4-difluoromethoxy-3-methoxy-phenyl)-2-(3,5-dichloro-pyridin-4-yl)-ethanone (CHF 5722).

Preparations of the Compounds of the Invention According to Method A

Example 7

Preparation of 2-(S)-(4-isobutyl-phenyl)-propionic acid 2-(3,5dichloro-pyridin-4-yl)-1-(3,4-dimethoxy-phenyl)vinyl ester (Z isomer=CHF 5480 and E isomer=CHF 5656)

A solution of 2-(3,5-dichloro-pyridin-4-yl)-1-(3,4-dimethoxy-phenyl)-ethanone (2.0 g, 6.2 mmol) in dry tetrahydrofuran (10 ml) was cooled down to −78° C. then a 1.8 M solution of lithium diisopropylamide in tetrahydrofuran (4.1 ml, 7.4 mmol) was added dropwise keeping the temperature below −70° C. The resulting solution was stirred for 30 min., then added with a solution of 2-(S)-(4-isobutyl-phenyl)-propionyl chloride (1.4 g, 6.4 mmol) in dry tetrahydrofuran (10 ml) and left to warm to room temperature. After stirring for further 30 min., the reaction was quenched with brine (20 ml) and water (50 ml) and the mixture was extracted with ethyl acetate (2×40 ml). The combined organic layers were dried over sodium sulphate and evaporated under reduced pressure to give an oil as mixture of Z and E isomers. These were separated by preparative HPLC water (water/acetonitrile=70/30 to 20/80).

1.0 g of the Z isomer was obtained as white solid.

MS/ESI$^+$ 514, 516 [MH]$^+$; $^1$H NMR (Acetone-d$^6$ calibrated at 2.05 ppm) δ0.88-0.98 (d, 6H), 1.30-1.38 (d, 3H), 1.78-2.00 (m, 1H), 2.45-2.53 (d, 2H), 3.73 (s, 3H), 3.78-3.92 (s+m, 4H), 6.74 (s, 1H), 6.88-6.94 (d, 1H), 7.00-7.12 (m, 6H), 8.41 (s, 2H).

400 mg of the E isomer were obtained as white solid.

$^1$H NMR (CDCl$_3$-d$^1$ calibrated at 7.26 ppm) δ0.90-0.93 (d, 6H), 1.56-1.60 (d, 3H), 1.77-1.97 (m, 1H), 2.45-2.49 (d, 2H), 3.42 (s, 3H), 3.79 (s, 3H), 3.87-3.94 (m, 1H), 6.12 (s, 1H), 6.36-6.56 (m, 3H), 7.10-7.14 (m, 2H), 7.23-7.28 (m, 2H), 8.41 (s, 2H).

Example 8

Preparation of 2-(R)-phenyl-propionic acid (Z)-2-(3, 5-dichloro-pyridin-4-yl)-1-(3,4-dimethoxy-phenyl) vinyl ester (CHF 5559)

The compound was obtained starting from 2-(R)-phenyl-propionyl chloride and 2-(3,5-dichloro-pyridin-4-yl)-1-(3,4-dimethoxy-phenyl) -ethanone, following the procedure of Example 7 (0.22 g, 0.48 mmol, 21% yield).

MS/ESI$^+$ 458, 460 [MH]$^+$; $^1$H NMR (Acetone-d$^6$ calibrated at 2.05 ppm) δ 1.30-1.40 (d, 3H), 3.71 (s, 3H), 3.77-3.97 (s+m, 4H), 6.73 (s, 1H), 6.88-6.98 (d, 1H), 7.01-7.06 (d, 1H), 7.08-7.14 (dd, 1H), 7.16-7.32 (m, 5H), 8.40 (s, 2H).

Example 9

Preparation of 2-(S)-(4-Isobutyl-phenyl)-propionic acid, (Z)-1-(3-cyclopentyloxy-4-methoxy-phenyl)-2-(3,5-dichloro-pyridin-4-yl)vinyl ester (CHF 5538) and 2-(S)-(4-Isobutyl-phenyl)-propionic acid, (E)-1-(3-cyclopentyloxy-4-methoxy-phenyl)-2-(3,5-dichloro-pyridin-4-yl)vinyl ester (CHF 5543)

The two isomers were obtained starting from 2-(S)-(4-isobutyl-phenyl) -propionylchloride and 1-(3-cyclopentyloxy-4-methoxy-phenyl)-2-(3,5-dichloro-pyridin -4-yl)-ethanone following the procedure of Example 7.

Z-isomer: MS/ESI$^+$ 568, 570 [MH]$^+$; $^1$H NMR (Acetone-d$^6$ calibrated at 2.05 ppm) δ 0.96-1.00 (d, 6H), 1.38-1.46 (d, 3H), 1.62-2.03 (m, 9H), 2.50-2.64 (d, 2H), 3.86-3.98 (s+m, 4H), 6.72 (s, 1H), 6.95-7.20 (m, 7H), 8.50 (s, 2H).

E-isomer; MS/ESI$^+$ 568, 570 [MH]$^+$; $^1$H NMR (Acetone-d calibrated at 2.05 ppm) δ0.90-0.93 (d, 6H), 1.52-1.56 (d, 3H), 1.83-1.93 (m, 1H), 2.49-2.53 (d, 2H), 3.72 (s, 3H), 3.99-4.10 (m, 1H), 4.20-4.29 (m, 1H), 6.19 (s, 1H), 7.10-7.14 (m, 2H), 7.18-7.34 (m, 5H), 8.50 (s, 2H).

Example 10

Preparation of 3,4-dimethoxy-benzoic acid (Z)-1-(3-cyclopropylmethoxy-4-methoxy-phenyl)-2-(3,5-dichloro-pyridin-4-yl)vinyl ester (CHF 5606)

The compound was obtained starting from 3,4-dimethoxy-benzoyl chloride and 1-(3-cyclopropylmethoxy-4-methoxy-phenyl)-2-(3,5-dichloro -pyridin-4-yl)-ethanone, following the procedure of Example 7.

MS/ESI$^+$ 530, 532 [MH]$^+$; $^1$H NMR (Acetone-d$^6$ calibrated at 2.05 ppm) δ 0.25-0.65 (2m, 4H), 1.12-1.38 (m, 1H), 3.80-3.95 (3s+dd, 11H), 6.88 (s, 1H), 6.96-7.10 (2d, 2H), 7.18-7.28 (d, 1H), 7.30-7.37 (d, 1H), 7.46-7.54 (d, 1H), 7.60-7.72 (d, 1H), 8.50 (s, 2H).

Example 11

Preparation of phenylacetic acid (Z)-1-(3-cyclopentyloxy-4-methoxy-phenyl) -2-(3,5-dichloro-pyridin-4-yl)vinyl ester (CHF 5605)

The compound was obtained starting from phenyl-acetyl chloride and 1-(3-cyclopentyloxy-4-methoxy-phenyl)-2-(3, 5-dichloro-pyridin-4-yl)-ethanone following the procedure of Example 7.

MS/ESI$^+$ 498, 500 [MH]$^+$; $^1$H NMR (Acetone-d$^6$ calibrated at 2.05 ppm) δ 1.50-1.95 (m, 8H), 3.72 (s, 2H), 3.84 (s, 3H), 4.68-4.82 (m, 1H), 6.72 (s, 1H), 6.93-7.01 (d, 1H), 7.07-7.11 (d, 1H), 7.13-7.20 (m, 3H), 7.21-7.32 (m, 3H), 8.44 (s, 2H).

Example 12

Preparation of 2-(S)-phenyl-propionic acid (Z)-2-(3, 5-dichloro-pyridin-4-yl)-1-(3,4-dimethoxy-phenyl) vinyl ester (CHF 5623)

The compound was obtained starting from 2-(S)-phenyl-propionyl chloride and 2-(3,5-dichloro-pyridin-4-yl)-1-(3,4-dimethoxy-phenyl) -ethanone, following the procedure of Example 7.

MS/ESI$^+$ 458, 460 [MH]$^+$; $^1$H NMR (Acetone-d$^6$ calibrated at 2.05 ppm), δ 1.31-1.39 (d, 3H), 3.71 (s, 3H), 3.80-3.96 (s+m, 4H), 6.73 (s, 1H), 6.89-6.97 (d, 1H), 7.07-7.11 (d, 1H), 7.08-7.14 (dd, 1H), 7.16-7.23 (m, 2H), 7.24-7.30 (m, 3H), 8.40 (s, 2H).

Example 13

Preparation of 3-benzyloxy-4-methoxy-benzoic acid (Z)-1-(3-cyclopentyloxy-4-methoxy-phenyl)-2-(3,5-dichloro-pyridin-4-yl)vinyl ester (CHF 5528)

The compound was obtained starting from 3-benzyloxy-4-methoxy-benzoyl chloride and 1-(3-cyclopentyloxy-4-methoxy-phenyl)-2-(3,5-dichloro -pyridin-4-yl)-ethanone, following the procedure of Example 7.

MS/ESI$^+$ 620, 622 [MH]$^+$; $^1$H NMR (Acetone-d$^6$ calibrated at 2.05 ppm) δ 1.11-1.95 (m, 8H), 3.85 and 3.92 (2s, 6H), 4.72-4.90 (m, 1H), 5.16 (s, 2H), 6.86 (s, 1H), 6.96-7.12 (m, 2H), 7.15-7.56 (m, 6H), 7.60-7.76 (d, dd, 2H), 8.48 (s, 2H).

Example 14

Preparation of 4-nitro-benzoic acid (Z)-2-(3,5-dichloro-pyridin-4-yl)-1-(3,4-dimethoxy-phenyl) vinyl ester (CHF 5513)

The compound was obtained starting from 4-nitro-benzoyl chloride and 2-(3,5-dichloro-pyridin-4-yl)-1-(3,4-dimethoxy-phenyl)-ethanone, following the procedure of Example 7.

MS/ESI$^+$ 475, 477 [MH]$^+$; $^1$H NMR (Acetone-d$^6$ calibrated at 2.05 ppm) δ 3.86 (s, 6H), 6.97 (s, 1H), 7.00-7.05 (d, 1H), 7.26-7.31 (dd, 1H), 7.39-7.40 (d, 1H), 8.26-8.40 (m, 4H), 8.49 (s, 2H).

Example 15

Preparation of 4-amino-benzoic acid (Z)-2-(3,5-dichloro-pyridin-4-yl)-1-(3,4-dimethoxy-phenyl) vinyl ester (CHF 5530)

4-Nitro-benzoic acid 2-(3,5-dichloro-pyridin-4-yl)-1-(3,4-dimethoxy-phenyl)vinyl ester (1.2 g, 2.5 mmol), obtained as described in Example 14, was dissolved in ethanol (20 ml) and sodium dithionite (1.7 g, 9.7 mmol) was dissolved in water (10 ml). The two solutions were mixed and stirred for 3 hours. The solution was evaporated under reduced pressure to a volume of 10 ml, water (30 ml) was added and the mixture was extracted with ethyl acetate (2×50 ml). The combined organic layers were dried and evaporated to give an oil that was purified by preparative HPLC (water/acetonitrile from 7/3 to 3/7 v:v).

1.05 grams of the title compound were obtained (2.35 mmol, 42% yield).

MS/ESI$^+$ 445, 447 [MH]$^+$; $^1$H NMR (CDCl$_3$ calibrated at 7.26 ppm) δ 3.85-3.90 (2s, 6H), 6.56 (s, 1H), 6.60-6.65 (d, 2H), 6.83-6.92 (d, 1H), 7.10-7.15 (d, 1H), 7.16-7.25 (dd, 1H), 7.80-7.90 (d, 2H), 8.43 (s, 2H).

Example 16

Preparation of 4-(4-fluoro-benzenesulfonylamino)-benzoic acid, (Z)-2-(3,5-dichloro-pyridin-4-yl)-1-(3,4-dimethoxy-phenyl)vinyl ester (CHF 5533)

4-Amino-benzoic acid (Z)-2-(3,5-dichloro-pyridin-4-yl)-1-(3,4-dimethoxy-phenyl)vinyl ester (0.55 g, 1.23 mmol) of Example 15, dissolved in dichloromethane (10 ml), was added with triethylamine (0.12 g, 1.23 mmol) and p-fluorobenzenesulfonyl chloride (0.24 g, 1.23 mmol). The solution was stirred for 30 min. at room temperature. Water (30 ml) was added and the product was extracted with ethyl acetate (2×30 ml). The combined organic layers were dried over sodium sulphate and evaporated under reduced pressure to give an oil that was purified by preparative HPLC (water/acetonitrile from 7/3 to 3/7 v:v).

0.27 grams of the title compound (0.45 mmol, 36% yield) were obtained.

MS/ESI$^+$ 603, 605 [MH]$^+$; $^1$H NMR (Acetone-d$^6$ calibrated at 2.05 ppm) δ 3.83-3.84 (2s, 6H), 6.87 (s, 1H), 6.95-7.00 (d, 1H), 7.16-7.26 (dd, 1H), 7.28-7.44 (m, 5H), 7.88-8.00 (m, 4H), 8.45 (s, 2H).

Example 17

Preparation of 4-(toluene-4-sulfonylamino)-benzoic acid, (Z)-2-(3,5-dichloro-pyridin-4-yl)-1-(3,4-dimethoxy-phenyl)vinyl ester (CHF 5537)

The compound was obtained starting from 4-toluenesulfonyl chloride and 4-amino-benzoic acid (Z)-2-(3,5-dichloro-pyridin-4-yl)-1-(3,4-dimethoxy-phenyl)vinyl ester, following the procedure of Example 16.

MS/ESI$^+$ 599, 601 [MH]$^+$; $^1$H NMR (Acetone-d$^6$ calibrated at 2.05 ppm) δ 2.38 (s, 3H), 3.83 and 3.84 (2s, 6H), 6.88 (s, 1H), 7.16-7.25 (dd, 1H), 7.28-7.42 (m, 5H), 7.58-7.84 (m, 3H), 7.86-7.96 (d, 2H), 8.45 (s, 2H), 9.15-9.98 (br, 1H).

Example 18

Preparation of 4-methanesulfonylamino-benzoic acid (Z)-2-(3,5-dichloro-pyridin-4-yl)-1-(3,4-dimethoxy-phenyl)vinyl ester (CHF 5526)

The compound was obtained starting from 4-methanesulfonyl chloride and 4-amino-benzoic acid (Z)-2-(3,5-dichloro-pyridin-4-yl)-1-(3,4-dimethoxy-phenyl)vinyl ester, following the procedure of Example 16.

MS/ESI$^+$ 523, 525 [MH]$^+$; $^1$H NMR (Acetone-d$^6$ calibrated at 2.05 ppm) δ 3.14 (s, 3H), 3.86 (s, 6H), 6.90 (s, 1H), 6.96-7.05 (d, 1H), 7.18-7.30 (dd, 1H), 7.32-7.49 (2d, 3H), 7.94-8.10 (d, 2H), 8.45 (s, 2H).

Example 19

Preparation of phenyl-acetic acid (Z)-2-(3,5-dichloro-pyridin-4-yl)-1-(3,4-dimethoxy-phenyl) vinyl ester (CHF 5558)

The compound was obtained starting from phenyl-acetyl chloride and 2-(3,5-dichloro-pyridin-4-yl)-1-(3,4-dimethoxy-phenyl)-ethanone following the procedure of Example 7.

MS/ESI$^+$ 444, 446 [MH]$^+$; $^1$H NMR (Acetone-d$^6$ calibrated at 2.05 ppm) δ 3.72 (s, 2H), 3.78-3.84 (2s, 6H), 6.75 (s, 1H), 6.94-7.00 (d, 1H), 7.12-7.22 (m, 4H), 7.23-7.32 (m, 3H), 8.44 (s, 2H).

Example 20

Preparation of 3-benzyloxy-4-methoxy-benzoic acid (Z)-2-(3,5-dichloro-pyridin-4-yl)-1-(3,4-dimethoxy-phenyl)vinyl ester (CHF 5542)

The compound was obtained starting from 3-benzyloxy-4-methoxy-benzoyl chloride and 2-(3,5-dichloro-pyridin-4-yl)-1-(3,4-dimethoxy-phenyl)-ethanone, following the procedure of Example 7.

MS/ESI$^+$ 566, 568 [MH]$^+$; $^1$H NMR (CDCl$_3$ calibrated at 7.26 ppm) δ 3.88-3.93 (3s, 9H), 5.14 (s, 2H), 6.57 (s, 1H), 6.82-6.95 (2d, 2H), 7.10-7.23 (d+dd, 2H), 7.28-7.50 (m, 5H), 7.56-7.62 (d, 1H), 7.68-7.78 (dd, 1H), 8.42 (s, 2H).

Example 21

Preparation of 4-methoxy-benzoic acid (Z)-2-(3,5-dichloro-pyridin-4-yl)-1-(3,4-dimethoxy-phenyl) vinyl ester (CHF 5429)

The compound was obtained starting from 4-methoxy-benzoyl chloride and 2-(3,5-dichloro-pyridin-4-yl)-1-(3,4-dimethoxy-phenyl)-ethanone, following the procedure of Example 7.

MS/ESI$^+$ 460, 462 [MH]$^+$; $^1$H NMR (Acetone-d$^6$ calibrated at 2.05 ppm) δ 3.85 and 3.86 and 3.89 (3s, 9H), 6.88 (s, 1H), 6.98-7.05 (m, 3H), 7.21-7.27 (dd, 1H), 7.36-7.34 (d, 1H), 7.97-8.01 (m, 2H), 8.47 (s, 2H).

Example 22

Preparation of 3-cyclopropylmethoxy-4-difluoromethoxy-benzoic acid (Z)-2-(3,5-dichloro-pyridin-4-yl)-1-(3,4-dimethoxy-phenyl)vinyl ester (CHF 5555)

The compound was obtained starting from 3-cyclopropylmethoxy-4-difluoromethoxy -benzoyl chloride and 2-(3,5-dichloro-pyridin-4-yl)-1-(3,4-dimethoxy -phenyl)-ethanone, following the procedure of Example 7.

MS/ESI$^+$ 566, 568 [MH]$^+$; $^1$H NMR (Acetone-d$^6$ calibrated at 2.05 ppm) δ 0.33-0.72 (2m, 4H), 1.20-1.42 (m, 1H), 3.85 and 3.87 (2s, 6H), 3.95-4.05 (d, 2H), 6.69-7.37 (t, 1H), 6.92 (s, 1H), 6.98-7.04 (d, 1H), 7.21-7.28 (m, 2H), 7.36-7.37 (d, 1H), 7.65-7.68 (m, 2H), 8.50 (s, 2H).

Example 23

Preparation of 1-p-tolyl-cyclopropanecarboxylic acid, (Z)-2-(3,5-dichloro -pyridin-4-yl)-1-(3,4-dimethoxy-phenyl)vinyl ester (CHF 5557)

The compound was obtained starting from 1-p-tolyl-cyclopropanecarbonyl chloride and 2-(3,5-dichloro-pyridin-4-yl)-1-(3,4-dimethoxy -phenyl)-ethanone, following the procedure of Example 7.

MS/ESI$^+$ 484, 490 [MH]$^+$; $^1$H NMR (Acetone-d$^6$ calibrated at 2.05 ppm) δ 1.10-1.43 (2m, 4H), 2.30 (s, 3H), 3.85 (s, 6H), 6.71 (s, 1H), 6.95-7.05 (d, 1H), 7.05-7.20 (m, 6H), 8.56 (s, 2H).

Preparation of the Compounds of the Invention According to Method B

Example 24

Preparation of benzoic acid, (Z)-2-(3,5-dichloro-pyridin-4-yl)-1-(3,4-dimethoxy-phenyl)vinyl ester (CHF 5415)

A solution of 3,5-dichloro-4-methyl-pyridine (1.0 g, 6.2 mmol) in dry tetrahydrofuran (10 ml) was cooled down to −78° C. then a 1.8 M solution of lithium diisopropylamide in tetrahydrofuran (7.0 ml, 12.5 mmol) was added dropwise keeping the temperature below −70° C. The resulting solution was stirred for 30 min., then added with a solution of 3,4-dimethoxy-benzoyl chloride (1.24 g, 6.2 mmol) in dry THF (10 ml) maintaining the temperature below −70° C. Benzoyl chloride (0.87 ml, 6.2 mmol) in dry tetrahydrofuran (10 ml) was added dropwise, over a period of 5 min, then the mixture was left to reach room temperature. After stirring for further 30 min., the reaction was quenched with water (100 ml) and the crude product was extracted with ethyl acetate (2×40 ml). The combined organic layers were dried over sodium sulphate and evaporated under reduced pressure to give an oil that was purified by flash chromatography (gradient mixture: petroleum ether/ethyl acetate from 9/1 to 7/3 v:v).

0.93 grams (2.16 mmol, 35% yield) of the title compound were obtained as a white solid.

MS/ESI$^+$ 430, 432 [MH]$^+$; $^1$H NMR (CDCl$_3$ calibrated at 7.26 ppm) δ 3.86 (s, 6H), 6.92 (s, 1H), 7.01-7.04 (d, 1H), 7.23-7.28 (dd, 1H), 7.37-7.38 (d, 1H), 7.62-7.75 (m, 4H), 8.02-8.03 (d, 1H), 8.49 (s, 2H).

Example 25

Preparation of 3,4-dimethoxy-benzoic acid (Z)-1-(3-cyclopropylmethoxy-4-difluoromethoxy-phenyl)-2-(3,5-dichloro-pyridin-4-yl)vinyl ester (CHF 5472), The compound was obtained starting from 3-cyclopropylmethoxy-4-difluoromethoxy -benzoyl chloride, 3,5-dichloro-4-methylpyridine and 3,4-dimethoxy-benzoyl chloride, following the procedure of Example 24.

MS/ESI$^+$ 566, 568 [MH]$^+$; $^1$H NMR (Acetone-d$^6$ calibrated at 2.05 ppm) δ 0.35-0.38 (m, 2H), 0.57-0.64 (m, 2H), 1.25-1.29 (m, 1H), 3.84-3.90 (2s, 6H), 3.99-4.02 (d, 2H), 6.60-7.36 (t, 1H), 6.98 (s, 1H), 7.03-7.08 (m, 1H), 7.27-7.29 (m, 2H), 7.49-7.52 (m, 2H), 7.64-7.69 (dd, 1H), 8.51 (s, 2H).

Example 26

Preparation of 3,4-dimethoxy-benzoic acid, (Z)-1-(3-cyclopentyloxy-4-methoxy-phenyl)-2-(3,5-dichloro-pyridin-4-yl)vinyl ester (CHF 5532)

The compound was obtained starting from 3-cyclopentyloxy-4-methoxy-benzoyl chloride, 3,5-dichloro-4-methylpyridine and 3,4-dimethoxy-benzoyl chloride, following the procedure of Example 24.

MS/ESI$^+$ 544, 546 [MH]$^+$; $^1$H NMR (Acetone-d$^6$ calibrated at 2.05 ppm) δ 1.48-1.92 (m, 8H), 3.85 (s, 6H), 3.90 (s, 3H), 4.77-4.92 (m, 1H), 6.86 (s, 1H), 6.98-7.10 (t, 2H), 7.22-7.30 (s+dd, 2H), 7.50-7.55 (d, 1H), 7.65-7.72 (dd, 1H), 8.50 (s, 2H).

Example 27

Preparation of 3-benzyloxy-benzoic acid (Z)-2-(3,5-dichloro-pyridin-4-yl)-1-(3,4-dimethoxy-phenyl) vinyl ester (CHF 5524)

The compound was obtained starting from 3,4-dimethoxy-benzoyl chloride, 3,5-dichloro-4-methylpyridine and 3-benzyloxy-benzoyl chloride, following the procedure of Example 24.

MS/ESI$^+$ 536, 538 [MH]$^+$.

Example 28

Preparation of Methyl-o-tolyl-carbamic acid (Z)-2-(3,5-dichloro-pyridin-4-yl)-1-(3,4-dimethoxy-phenyl)vinyl ester (CHF 5550)

A solution of 2-(3,5-dichloro-pyridin-4-yl)-1-(3,4-dimethoxy -phenyl)-ethanone (2.0 g, 6.2 mmol) in dry tetrahydrofuran (10 ml) was cooled to −78° C. then a 1.8 M solution of lithium diisopropylamide in tetrahydrofuran (4.1 ml, 7.4 mmol) was added dropwise keeping the temperature below −70° C. The resulting solution was stirred for 30 min., then added with a solution of methyl-o-tolyl-carbamoyl chloride (1.1 g, 6.8 mmol) in dry tetrahydrofuran (10 ml) and left to warm to room temperature. After stirring for 30 min. the reaction was quenched with water (100 ml) and the crude product was extracted with ethyl acetate (2×40 ml). The combined organic layers were dried over sodium sulphate and evaporated under reduced pressure to give an oil that was purified by flash chromatography (eluent: ethyl acetate/petroleum ether from 10/90 to 30/70 v:v).

1.6 g (3.4 mmol, 55% yield) of the title compound was obtained as a white solid.

MS/ESI⁺ 473, 475 [MH]⁺; ¹H NMR (DMSO-d₆ calibrated at 2.5 ppm) δ 2.98 (s, 3H), 3.14 (s, 3H), 3.75-3.95 (2s, 6H), 6.72 (s, 1H), 6.78-6.88 (d, 1H), 7.00-7.40 2m, 6H), 8.57 (s, 2H).

Example 29

Preparation of (3,4-dimethoxy-phenyl)-carbamic acid, (Z)-1-(3-cyclopropylmethoxy-4-difluoromethoxy-phenyl)-2-(3,5-dichloro-pyridin-4-yl) vinyl ester (CHF 5522)

The compound was obtained starting from 3,4-dimethoxy-phenyl-isocyanate and
1-(3-cyclopropylmethoxy-4-difluoromethoxy-phenyl)-2-(3,5-dichloro-pyridin-4-yl)-ethanone, following the procedure of Example 28.

MS/ESI⁺ 581, 583 [MH]⁺.

Example 30

Preparation of methyl-phenyl-carbamic acid (Z)-2-(3,5-dichloro-pyridin-4-yl)-1-(3,4-dimethoxy-phenyl)vinyl ester (CHF 5574)

The compound was obtained starting from methyl-phenyl-carbamoyl chloride and 2-(3,5-dichloro-pyridin-4-yl)-1-(3,4-dimethoxy-phenyl)-ethanone, following the procedure of Example 28.

MS/ESI⁺ 459, 461 [MH]⁺; ¹H NMR (Acetone-d⁶ calibrated at 2.05 ppm) δ 3.16-3.30 (br, s, 3H), 3.82 and 3.92 (2s, 6H), 6.68 (s, 1H), 6.95-7.05 (d, 1H), 7.14-7.44 (m+dd, 7H), 8.54 (s, 2H).

Preparation of "Symmetric" Derivatives According To a Simplified Version of Method B Example 31

Preparation of 3-cyclopropylmethoxy-4-difluoromethoxy-benzoic acid (Z)-1-(3-cyclopropylmethoxy-4-difluoromethoxy-phenyl)-2-(3,5-dichloro-pyridin-4-yl)vinyl ester (CHF 5514)

A solution of 3,5-dichloro-4-methyl-pyridine (2.06 g, 12.7 mmol) in dry tetrahydrofuran (30 ml) was cooled down to −78° C. then a 1.8 M solution of lithium diisopropylamide in tetrahydrofuran (14.8 ml, 26.7 mmol) was added dropwise keeping the temperature below −70° C. The resulting solution was stirred for 30 min, then added with a solution of 3-cyclopropylmethoxy-4-difluoromethoxybenzoyl chloride (7.02 g, 25.4 mmol) in dry tetrahydrofuran (20 ml) and left to warm to room temperature. After stirring for further 30 min., the reaction was quenched with water (300 ml) and extracted with ethyl acetate (3×50 ml). The combined organic solutions were dried over sodium sulphate and evaporated under reduced pressure to give an oil that was purified by flash chromatography (eluent: petroleum ether/ethyl acetate=9/1 to 7/3 v:v).

2.4 g (3.8 mmol, 30% yield) of the title compound were obtained as a white solid.

MS/ESI⁺ 642, 644 [MH]⁺; ¹H NMR (Acetone-d⁶ calibrated at 2.05 ppm) δ 0.35-0.42 (m, 4H), 0.58-0.65 (m, 4H), 1.25-1.32 (m, 2H), 3.97-4.03 (m, 4H), 6.61-7.36 (t, 1H), 6.69-7.44 (t, 1H), 7.04 (s, 1H), 7.21-7.29 (m, 2H), 7.32 (m, 1H), 7.52-7.53 (d, 1H), 7.64-7.69 (m, 2H), 8.52 (s, 2H).

Example 32

Preparation of 3,4-Dimethoxy-benzoic acid, (Z)-2-(3,5-dichloro-pyridin-4-yl)-1-(3,4-dimethoxy-phenyl)-vinyl ester (CHF 5405)

The compound was obtained starting from 3,5-dichloro-4-methyl-pyridine and 3,4-dimethoxy-benzoyl chloride, following the procedure of Example 31.

MS/ESI⁺ 490, 492 [MH]⁺; ¹H NMR (Acetone-d⁶ calibrated at 2.05 ppm) δ 3.85 (s, 12H), 6.89 (s, 1H), 6.99-7.07 (t, 2H), 7.21-7.27 (dd, 1H), 7.36-7.52 (dd, 2H), 7.66-7.71 (dd, 1H), 8.49 (s, 2H).

Example 33

Preparation of 3-cyclopentyloxy-4-methoxy-benzoic acid, (Z)-1-(3-cyclopentyloxy-4-methoxy-phenyl)-2-(3,5-dichloro-pyridin-4-yl)vinyl ester (CHF 5408)

The compound was obtained starting from 3,5-dichloro-4-methyl-pyridine and 3-cyclopentyloxy-4-methoxybenzoyl chloride following the procedure of Example 31.

MS/ESI⁺ 598, 600 [MH]⁺; ¹H NMR (Acetone-d⁶ calibrated at 2.05 ppm) δ1.50-1.99 (m, 16H), 3.85 and 3.88 (2s, 6H), 4.80-4.88 (m, 2H), 6.86 (s, 1H), 7.00-7.07 (m, 2H), 7.25-7.30 (m, 2H), 7.52-7.53 (d, 1H), 7.62-7.68 (dd, 1H), 8.49 (s, 2H).

Example 34

Preparation of 3-cyclopropylmethoxy-4-methoxy-benzoic acid (Z)-1-(3-cyclopropylmethoxy-4-methoxy-phenyl)-2-(3,5-dichloro-pyridin-4-yl)vinyl ester (CHF 5546)

The compound was obtained starting from 3,5-dichloro-4-methyl-pyridine and 3-(cyclopropylmethoxy)-4-methoxybenzoyl chloride, following the procedure of Example 31.

MS/ESI⁺ 570, 572 [MH]⁺; ¹H NMR (Acetone-d⁶ calibrated at 2.05 ppm) δ 0.31-0.39 (m, 4H), 0.52-0.62 (m, 4H), 1.20-1.29 (m, 2H) 3.87-3.90 (2s+m, 10H), 6.86 (1s, 1H), 6.96-7.08 (t, 2H), 7.21-7.29 (dd, 1H), 7.30-7.36 (d, 1H), 7.45-7.50 (d, 1H), 7.62-7.70 (dd, 1H), 8.47 (s, 2H).

Example 35

Preparation of 4-Cyclopentyloxy-3-difluoromethoxy-benzoic acid, (Z)-1-(4-cyclopentyloxy-3-difluoromethoxy-phenyl) 2-(3,5-dichloro-pyridin-4-yl)vinyl ester (CHF 5517)

The compound was obtained starting from 3,5-dichloro-4-methyl-pyridine and 4-(cyclopentyloxy)-3-(difluoromethoxy)-benzoyl chloride following the procedure of Example 31.

MS/ESI⁺ 670, 672 [MH]⁺; ¹H NMR (Acetone-d⁶ calibrated at 2.05 ppm) δ 1.48-2.02 (m, 16H), 4.88-5.04 (m, 2H), 6.53-7.27 (t, 1H), 6.61-7.35 (t, 1H), 7.04 (s, 1H), 7.22-7.34 (d+m, 3H), 7.44-7.50 (d, 1H), 7.60-7.72 (d+m, 2H), 8.53 (s, 2H).

Example 36

Preparation of 3-Cyclopropylmethoxy-4-difluoromethoxy-benzoicacid, (Z)-1-(3-cyclopropylmethoxy-4-difluoromethoxy-phenyl)-2-(3,5-dichloro-1-oxy-pyridin-4-yl)vinyl ester (CHF 5649)

3-cyclopropylmethoxy-4-difluoromethoxy-benzoic acid (Z)-1-(3-cyclopropylmethoxy-4-difluoromethoxy-phenyl)-

2-(3,5-dichloro-pyridin-4-yl)vinyl ester (642 mg, 1 mmol) was dissolved in chloroform (20 mL) and added with m-chloroperbenzoic acid (0.5 g, 3 mmol) and the solution was kept at 0° C. for 24 hours.

The reaction was quenched with 1 N NaOH solution and the product was extracted with chloroform (2×50 mL). The combined organic solution was dried and evaporated under vacuum to afford a crude product that was purified by Preparative HPLC.

350 mg (0.53 mmol, 53% yield) of a white solid was obtained.

MS/ESI$^+$ 658, 660 [MH]$^+$; $^1$H NMR (DMSO-d$^6$ calibrated at 2.50 ppm) δ 0.32-0.97 (m, 4H), 0.55-0.59 (m, 4H), 1.16-1.29 (m, 2H), 3.93-3.99 (t, 2H), 6.12 (s, 1H), 6.74-7.49 (t, 1H, CHF$_2$), 6.88-7.62 (t, 1H, CHF$_2$), 7.09 (s, 1H), 7.12-7.25 (m, 3H), 7.35-7.30 (m, 1H), 7.47-7.49 (m, 1H), 7.59-7.66 (m, 2H), 8.59 (s, 2H).

Legend

NMR: nuclear magnetic resonance s=singlet; d=doublet; t=triplet; q=quartet; dd=doublet of doublets; m=multiplet; br=broad MS/ESI$^+$: Mass analysis using an electrospray source in the positive mode.

Pharmacological Activity of the Compounds of the Invention

Example 37

In Vitro Determination of PDE4 Inhibitory Activity in the Cell Free Assay

The U937 human monocytic cell line was used as source of PDE4 enzyme. Cells were cultured, harvested and supernatant fraction prepared essentially as described in Torphy T J et al J. Pharmacol. Exp. Ther. 1992; 263:1195-1205.

PDE4 activity was determined in cells supernatants by assaying cAMP disappearance from the incubation mixtures. 50 µl of cell supernatant were incubated at 30° C. for 30 minutes in a final volume of 200 µl in the presence of 1.6 µM cAMP with or without the test compound (50 µl).

The concentration of the test compounds ranged between $10^{-12}$ M and $10^{-6}$ M. Reactions were stopped by heat inactivation (2.5 minutes at 100° C.) and residual cAMP was measured using an electro-chemiluminescence (ECL)-based immunoassay.

The results, expressed as mean ±95% confidence limits of the molar concentration of the test compound producing 50% inhibition of cAMP disappearance (IC$_{50}$) are reported in Table 1 of Example 38.

Percentage of inhibition of PDE4 activity was calculated, assuming cAMP disappearance in the absence of inhibitors as 100% and cAMP disappearance in heat inactivated samples as 0%.

All the IC$_{50}$ values of the tested compounds, representative of the invention, were less than 0.2 microM.

Example 38

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α) release in peripheral blood mononuclear cells (PBMCs), was performed according to a method previously described (Hatzelmann A et al J. Pharmacol. Exp. Ther. 2001; 297:267-279; Draheim R et al J. Pharmacol. Exp. Ther. 2004; 308:555-563.

Cryopreserved human PBMCs, (100 µl/well) were incubated in 96-well plates (10$^5$ cells/well), for 30 min, in the presence or absence (50 microl) of the test compounds whose concentrations ranged from $10^{-12}$ M to $10^{-6}$ M. Subsequently, LPS (3 ng/ml) was added.

After 18 h incubation at 37° C. in a humidified incubator under an atmosphere of 95% air and 5% CO$_2$, culture medium was collected and TNF-α measured by ELISA.

The results, expressed as mean ±95% confidence limits of the molar concentration of the test compound producing 50% inhibition of LPS-induced TNF-α release (IC$_{50}$) are reported in Table 1.

The effects of the tested compounds were calculated as percentage of inhibition of TNF-α release, assuming LPS-induced TNF-α production in the absence of inhibitor compound as 100% and basal TNF-α production of PBMCs in the absence of LPS as 0%.

Even in this case, all the IC$_{50}$ values of the tested compounds were less than 0.2 microM.

TABLE 1

In vitro PDE4 inhibition activity of representative compounds of the invention

| Compound | IC$_{50}$ cell free microM | IC$_{50}$ PBMCS microM |
|---|---|---|
| CHF 5408 | 0.0013 (0.00074-0.0022) | 0.0009 (0.0003-0.0026) |
| CHF 5415 | 0.0057 (0.0031-0.0105) | 0.0057 (0.0029-0.0113) |
| CHF 5472 | 0.004 (0.003-0.005) | 0.0054 (0.0028-0.010) |
| CHF 5480 | 0.0179 (0.0132-0.0242) | 0.026 (0.012-0.056) |
| CHF 5429 | 0.001 (0.0006-0.0017) | 0.0056 (0.0013-0.023) |
| CHF 5513 | 0.0005 (0.00023-0.0011) | 0.0085 (0.0049-0.015) |
| CHF 5514 | 0.0012 (0.00097-0.0015) | 0.0125 (0.0015-0.107) |
| CHF 5526 | 0.0007 (0.0005-0.001) | 0.00377 (0.0023-0.0061) |
| CHF 5528 | 0.0073 (0.005-0.009) | 0.0218 (0.0065-0.0728) |
| CHF 5530 | 0.0017 (0.0009-0.0033) | 0.0054 (0.002-0.0144) |
| CHF 5533 | 0.00037 (0.00015-0.0009) | 0.0031 (0.0006-0.0155) |
| CHF 5537 | 0.00035 (0.00023-0.00054) | 0.0063 (0.0022-0.0177) |
| CHF 5546 | −0.0004 (0.0001-0.001) | 0.0010 (0.0005-0.002) |
| CHF 5532 | 0.0126 (0.006-0.0258) | 0.0022 (0.0012-0.0041) |
| CHF 5555 | 0.0061 (0.0042-0.0086) | 0.002 (0.0014-0.0029) |
| CHF 5557 | 0.0138 (0.0104-0.0184) | 0.0101 (0.0032-0.0318) |

Example 39

Evaluation of the Ability to Inhibit the Low Affinity LPDE4 Versus the Ability to Compete for the High Affinity HPDE4

The affinity toward LPDE4 and HPDE4 was assessed as previously described respectively in Cortijo J et al *Br J Pharmacol* 1993, 108: 562-568 and Duplantier A J et al *J Med Chem* 1996; 39: 120-125.

The activity of a representative compound of the invention, e.g. CHF 5408, was evaluated in comparison to the corresponding ketone, e.g. a compound lacking of the A substituent, hereinafter identified with the internal code CHF 5400.

The concentration of the test compounds ranged between $10^{-12}$ M and $10^{-5}$ M.

The results in terms of IC$_{50}$ are reported in Table 2.

In the case of LPDE4, the IC$_{50}$ is the molar concentration of the test compound producing 50% inhibition of cAMP disappearance, while in the case of HPDE4, the IC$_{50}$ is the molar concentration of the test compound producing 50% inhibition of the binding of [H$^3$] rolipram.

The results indicate that the compound of the invention inhibited LPDE4 with nanomolar affinity and was about 58-fold more selective toward LPDE4 versus HPDE4.

On the contrary, the corresponding ketone CHF 5400 inhibited LPDE4 and HPDE4 with a similar potency.

TABLE 2

Activity profiles of CHF 5408 and CHF 5400

| Compound | HPDE4 $IC_{50}$ (nM) | LPDE4 $IC_{50}$ (nM) | HPDE4/LPDE4 |
|---|---|---|---|
| CHF 5408 | 0.74 | 42.6 | 57.6 |
| CHF 5400 | 0.61 | 0.94 | 1.5 |

Example 40

In Vivo Determination of the Activity after Intratracheal Administration in an Animal Model of COPD The airway pathology of lipopolysaccharide (LPS)-induced acute pulmonary inflammation in rats, notably neutrophilia, resembles chronic obstructive pulmonary disease (COPD). The anti-inflammatory activity of a representative compound of the invention, e.g. CHF 5480 was evaluated after intratracheal (i.t.) administration according to the method described in Belvisi M G *J Pharmacol Exp Ther* 2005, 314: 568-574.

LPS inhalation resulted in an acute inflammatory response characterised by a massive pulmonary infiltration of neutrophils 4 h after treatment.

CHF 5480 was tested by i.t. instillation 24 h and 1 h before exposure to LPS. The i.t. treatment with CHF 5480 at doses ranging form 0.001 and 10 μmoles/kg caused a significant and dose-dependent inhibition of bronchoalveolar lavage neutrophils.

Maximal effect was observed at the 1 μmole/kg dose, with a reduction of neutrophilia by 60%. Moreover CHF 5480 exhibited sustained pulmonary levels in the lungs with mean residence time of 15.26 h, while no detectable levels were found in plasma.

The results indeed demonstrated that the compounds of the invention can be efficacious topically after administration by inhalation as well as they are endowed with a long pulmonary persistency and a short systemic action.

The invention claimed is:

1. A compound of general formula (I)

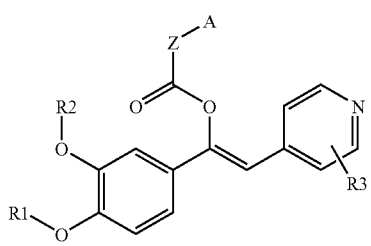

(I)

wherein

Z is selected from the group consisting of
(CH$_2$)$_n$ wherein n=0,1, or 2;
NR$_6$ wherein R$_6$ is H or a linear or branched C$_1$-C$_6$ alkyl;
CR$_4$R$_5$ wherein
R$_4$ is independently selected from the group consisting of H or a linear or branched C$_1$-C$_4$ alkyl, and
R$_5$ is independently selected from the group consisting of linear or branched C$_1$C$_4$ alkyl;

otherwise when R$_4$ and R$_5$ are both linear or branched C$_1$-C$_4$ alkyl they form a ring with the carbon atom they are linked to having 3, 4, 5 or 6 carbon atoms, R$_1$ and R$_2$ are the same or different and are independently selected from the group consisting of linear or branched C$_1$-C$_6$ alkyl, optionally substituted with one or more substituents selected form the group consisting of C$_3$-C$_7$ cycloalkyl and halogen; and C$_3$-C$_7$ cycloalkyl;

R$_3$ is one or more halogen atoms;

A is an optionally substituted phenyl in which the optional substituent R$_x$ can be one or more, may be the same or different, and is independently selected from the group consisting of:

linear or branched C$_1$-C$_6$ alkyl, optionally substituted with one or more with one or more substituents selected form the group consisting of C$_3$-C$_7$ cycloalkyl;

C$_3$-C$_7$ cycloalkyl;

OR$_7$ wherein R$_7$ is selected from the group consisting of H, linear or branched C$_1$-C$_6$ alkyl wherein the C$_1$-C$_6$ alkyl group can be unsubstituted or substituted by one or more substituents selected from the group consisting of C$_3$-C$_7$ cycloalkyl; phenyl, benzyl and halogen NR$_{10}$R$_{11}$ wherein R$_{10}$ and R$_{11}$ are and HNSO$_2$R$_{12}$ wherein R$_{12}$ is C$_1$-C$_6$alkyl or a phenyl optionally substituted with halogen atoms or with a C$_{1-4}$ alkyl group.

2. The compound of claim 1, wherein A is an optionally substituted phenyl.

3. The compound of claim 1, wherein R$_3$ is a halogen atom.

4. The compound of claim 3, wherein R$_3$ is chlorine.

5. The compound of claim 4 having general formula (II)

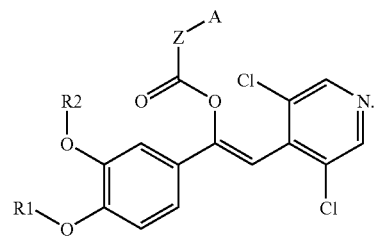

(II)

6. The compound of claim 5, wherein Z is (CH$_2$)$_n$ wherein n is 0 and A is optionally substituted phenyl.

7. The compound of claim 5, wherein Z is CHR$_5$, where R$_5$ is linear or branched C$_1$-C$_4$ alkyl; and A is optionally substituted phenyl.

8. The compound of claim 5, wherein Z is CR$_4$R$_5$ where R$_4$ and R$_5$ are both linear or branched C$_1$-C$_4$ alkyl and they form a ring with the carbon atom they are linked to having 3, 4, 5 or 6 carbon atoms; and A is optionally substituted phenyl.

9. A pharmaceutical composition containing the compounds of claim 1, as active ingredient in admixture with pharmaceutically acceptable carriers and/or excipients.

10. The pharmaceutical composition of claim 9, for administration by inhalation.

11. The pharmaceutical composition of claim 9 wherein said composition further comprises an additional active ingredient selected from the classes of beta2-agonists, corticosteroids and anticholinergic and antimuscarinic agents.

12. A pharmaceutical composition according to claim 9, wherein the dosage of the compound of general formula (I) is comprised between 0.01 and 1000 mg/day.

13. A compound as claimed in claim 1 wherein Z is methyl.

14. A compound as claimed in claim 1 wherein $R_4$ and $R_5$ form a ring with the carbon atom they are linked to having 3 carbon atoms.

15. The compound of claim 7, wherein Z is $CHR_5$, where $R_5$ is methyl.

16. The compound of claim 8, wherein Z is $CR_4R_4R_5$ where $R_4$ and $R_5$ are both linear or branched $C_1$-$C_4$ alkyl and they form a ring with the carbon atom they are linked to having 3, carbon atoms.

* * * * *